United States Patent
Yaoi (10) Patent No.: US 8,306,182 B2
(45) Date of Patent: Nov. 6, 2012

(54) X-RAY CT APPARATUS AND X-RAY DETECTING APPARATUS THEREOF

(75) Inventor: Yoshiaki Yaoi, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 305 days.

(21) Appl. No.: 12/719,687

(22) Filed: Mar. 8, 2010

(65) Prior Publication Data

US 2010/0232567 A1 Sep. 16, 2010

(30) Foreign Application Priority Data

Mar. 6, 2009 (JP) ................. P2009-053983

(51) Int. Cl.
*H05G 1/64* (2006.01)
(52) U.S. Cl. ............. 378/19; 378/98.8; 250/370.09
(58) Field of Classification Search ......... 378/19, 378/98.8; 250/370.09
See application file for complete search history.

(56) References Cited

U.S. PATENT DOCUMENTS

| | | | | |
|---|---|---|---|---|
| 5,991,357 A * | 11/1999 | Marcovici et al. | ........... | 378/19 |
| 6,115,448 A * | 9/2000 | Hoffman | ................ | 378/19 |
| 6,396,898 B1 * | 5/2002 | Saito et al. | ............... | 378/19 |
| 6,403,964 B1 * | 6/2002 | Kyyhkynen | ......... | 250/370.09 |
| 6,510,195 B1 * | 1/2003 | Chappo et al. | ............ | 378/19 |
| 6,522,715 B2 * | 2/2003 | Hoffman et al. | ........... | 378/19 |
| 6,587,538 B2 * | 7/2003 | Igarashi et al. | ............ | 378/19 |
| 6,671,345 B2 * | 12/2003 | Vrettos et al. | ............. | 378/19 |
| 6,717,150 B2 * | 4/2004 | Hoffman | ............... | 250/370.11 |
| 6,873,678 B2 * | 3/2005 | Hoffman | .................. | 378/19 |
| 6,917,664 B2 * | 7/2005 | Chappo et al. | ............ | 378/19 |
| 6,925,142 B2 * | 8/2005 | Pohan et al. | ............... | 378/19 |
| 6,982,423 B2 * | 1/2006 | Elgali | ................... | 250/370.11 |
| 7,010,088 B2 * | 3/2006 | Narayanaswamy et al. | .... | 378/91 |
| 7,075,089 B2 * | 7/2006 | Pohan | ................. | 250/370.09 |
| 7,161,157 B2 * | 1/2007 | Lacey | ................. | 250/370.15 |
| 7,177,387 B2 * | 2/2007 | Yasunaga et al. | .......... | 378/19 |
| 7,190,759 B2 * | 3/2007 | Ratzmann | ................. | 378/19 |
| 7,235,790 B2 * | 6/2007 | Hoge | ................. | 250/370.11 |
| 7,465,931 B2 * | 12/2008 | Vogtmeier et al. | ........ | 250/370.09 |
| 7,489,516 B2 * | 2/2009 | Lacey | .................... | 361/759 |
| 7,492,857 B2 * | 2/2009 | Yasunaga et al. | .......... | 378/19 |
| 7,522,699 B2 * | 4/2009 | Pohan et al. | ............... | 378/19 |
| 7,560,702 B2 * | 7/2009 | Meirav et al. | ............. | 250/370.13 |
| 7,564,940 B2 * | 7/2009 | Mattson et al. | ............ | 378/19 |
| 7,576,330 B1 * | 8/2009 | Lacey et al. | ............. | 250/370.15 |
| 7,627,086 B2 * | 12/2009 | Vogtmeier | ................ | 378/98.8 |
| 7,728,298 B2 * | 6/2010 | Heismann | ............. | 250/363.05 |

FOREIGN PATENT DOCUMENTS

JP 2005-283441 10/2005

* cited by examiner

*Primary Examiner* — Allen C. Ho
(74) *Attorney, Agent, or Firm* — Oblon, Spivak, McClelland, Maier & Neustadt, L.L.P.

(57) ABSTRACT

A high-resolution X-ray apparatus and a high-resolution X-ray detecting apparatus includes a plurality of multi-slice X-ray detection packs held on the pair of guide rails by detachable tight fitting members. A detachable pressing board is provided on the pair of guide rails for fixing the plurality of detection packs so that edges of adjacent detection packs contact each other.

9 Claims, 8 Drawing Sheets

X-RAY CT APPARATUS AND X-RAY DETECTING APPARATUS THEREOF

CROSS-REFERENCE TO RELATED APPLICATIONS

This application claims priority under 35 U.S.C. §119(a) from, and the benefit of, Japanese Patent Application No. 2009-53983 filed on Mar. 6, 2009, the contents of which are expressly incorporated herein by reference in their entirety.

BACKGROUND OF THE INVENTION

A. Field of the Invention

The present invention relates to an X-ray computer tomography (CT) apparatus and an X-ray detection apparatus thereof, and more particularly, to a high-resolution X-ray apparatus and a high-resolution X-ray detecting apparatus including a plurality of X-ray detection packs that are detachably arranged in an X-ray scanning direction.

B. Background of the Invention

An X-ray CT apparatus reconstructs tomography images based on projection data acquired from various directions by scanning around an object. Usually, an X-ray tube and a detection unit are supported on a rotation frame in a gantry of an X-ray CT apparatus. The X-ray tube and the detection unit are positioned so as to face each other. In the rotation frame, a high voltage generating apparatus is also supported for supplying a high voltage to the X-ray tube.

The X-rays emitted from the X-ray tube and penetrated through the object are detected by the X-ray detection unit. The X-ray detection unit includes multiple X-ray detection elements arranged in a circular arc-shape so as to face the X-ray tube. It is impossible to construct such a circular arc-shaped detection unit in an integrated architecture. Accordingly, it has conventionally been proposed to construct the X-ray detection unit by dividing the multiple X-ray detection elements into a plurality of detection packs arranged in a rotation direction (channel direction) of the rotation frame in the gantry (For instance, see Japanese Patent Application Publication 2005-283441).

In each of the plurality of detection packs, a plurality of detecting elements are arranged in the channel direction at a prescribed channel pitch. To remove a detection pack for maintenance, a gap has conventionally been provided between each of two detection packs in the X-ray detection unit. The gap is sufficiently smaller than a channel pitch of each detecting element in each detection pack. Since the gap provided between the two detection packs arranged next to each other has conventionally been made sufficiently smaller than the channel pitch of each detecting element, acquisition of projection data has not been a problem.

However, recently, a high-resolution detection pack has been developed by providing a plurality of high-resolution detecting elements for increasing resolution of the X-ray CT image by reducing the channel pitch of the conventional detecting element in each of the detection packs. In such a high-resolution detection pack, the channel pitch of each detecting element has become much narrower than in the conventional detection pack. Consequently, the conventional gap provided between two detection packs has relatively increased compared to the channel pitch of each high-resolution detecting element. For instance, each of the conventional gaps provided between two detection packs becomes almost equal to the channel pitch of the high-resolution detecting element. As a result, X-ray penetrated through an object cannot be detected at positions corresponding to the gaps provided between each of two detection packs. Thus, the projection data acquired from the high-resolution detection pack is missing a data channel corresponding to each of the gaps between the multi-slice detecting elements, which creates a serious problem in reduced resolution of the acquired image data.

SUMMARY OF THE INVENTION

The present invention addresses the abovementioned problems and defects of the conventional X-ray CT apparatus and X-ray detecting apparatus and provides an improved high-resolution X-ray apparatus and a high-resolution X-ray detecting apparatus thereof that can eliminate the lack of projection data corresponding to the gaps provided between the multi-slice detecting elements in each of the X-ray detection packs. Further, the X-ray CT apparatus and X-ray detecting apparatus consistent with the present invention can easily perform maintenance of the X-ray detection packs by moving the X-ray detection packs along a pair of rail guides.

According to one aspect of the present invention, there is provided an X-ray CT apparatus including:

an X-ray source provided in a gantry so as to irradiate X-ray beam on an object placed at a center position of the gantry;

a multi-slice X-ray detection unit provided in the gantry and located opposite the X-ray source so as to detect X-ray amounts penetrated through the object;

wherein the multi-slice X-ray detection unit includes, a plurality of detection pack units successively arranged along a channel direction of the X-ray beam to detect X-rays penetrated through the object, a pair of guide rails configured to freely move the plurality of detection packs along the channel direction, and a fixing unit detachably held by the pair of guide rails to fix the plurality of detection packs so that adjacent edges of said detection packs contact each other.

According to another aspect of the present invention, there is provided an X-ray detecting apparatus for detecting X-ray amounts penetrated through an object by irradiating an X-ray beam on the object, the X-ray detecting apparatus including:

a plurality of detection packs successively arranged in an arrangement direction and configured to detect the X-ray amounts penetrated through the object;

a pair of guide rails configured to hold the plurality of detection packs so as to freely move each of the detection packs along the arrangement direction of the packs; and a fixing unit provided on each of the guide rails to fix the plurality of detection packs that adjacent edges of said detection packs contact each other.

According to the X-ray detecting apparatus consistent with the present invention, a plurality of detection packs are arranged so as that adjacent detection packs contact each other along an arrangement direction so as to eliminate gaps existing between the adjacent detection packs. Due to the contacting arrangement of the detection packs, it becomes difficult to easily exchange the detection packs for maintenance. For instance, to change a detection pack at a center portion of the X-ray detecting apparatus, a plurality of detection packs must be successively removed from the detection pack positioned at the far edge sides relative to a target detection pack to be removed. This deteriorates efficiency of the maintenance operation. To avoid this problem, the X-ray detecting apparatus according to the present invention provides a pair of guide rails at both sides in a scan direction of the detection pack in order to freely hold the plurality of detection packs between the pair of the guide rails. During X-ray projection data acquisition, the plurality of detection packs are fixed with adjacent edges of the detection packs in contact so as to eliminate the gap provided between the conventional two detection packs. On the other hand, for a maintenance operation, the detection packs can be easily moved along the guide rails in order to generate a gap between the two detection packs for removing a target detection pack.

BRIEF DESCRIPTION OF THE DRAWINGS

The accompanying drawings, which are incorporated in and constitute part of this specification, illustrate various embodiments and/or features of the present invention, and together with the description, serve to explain the present invention. Where possible, the same reference number will be used throughout the drawings to describe the same or like parts. In the drawings.

DESCRIPTION OF THE EMBODIMENTS

Figure 1:
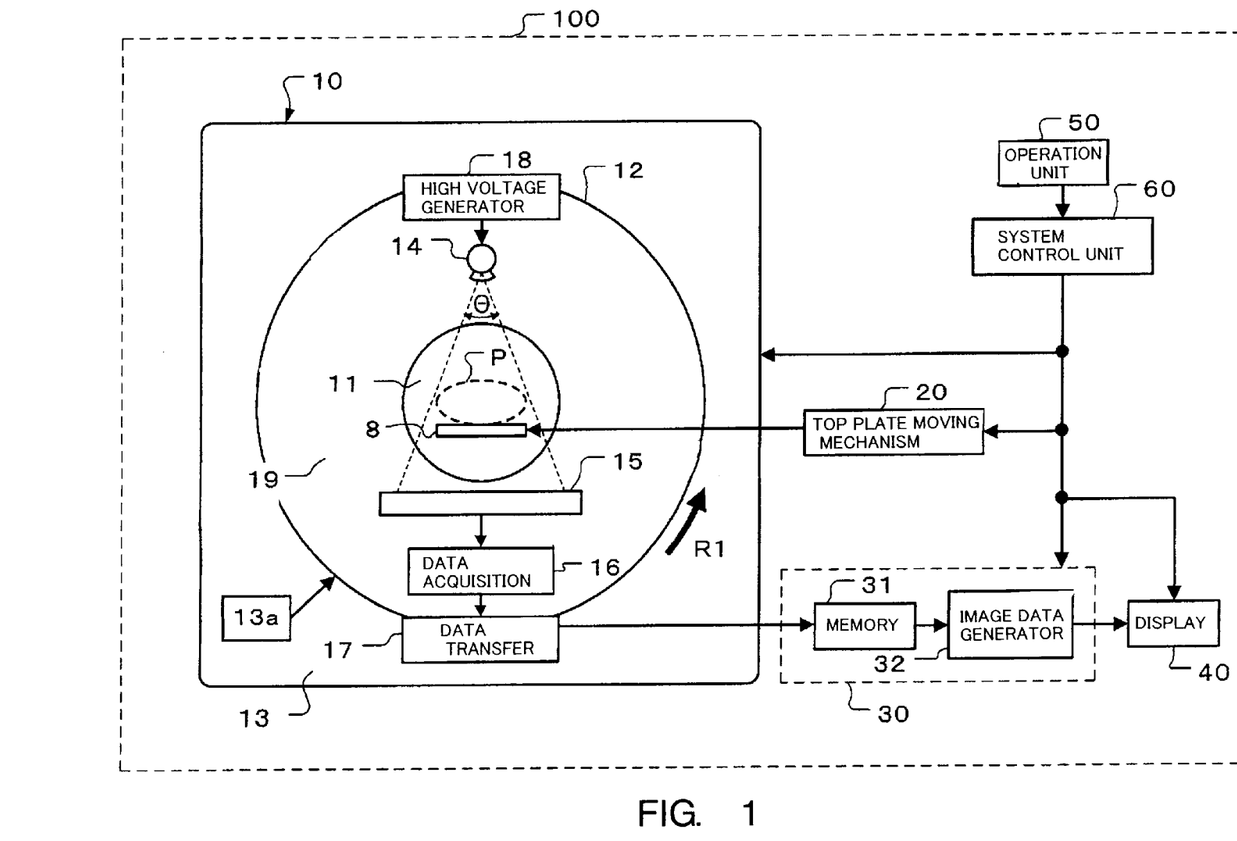
FIG. 1 is a block diagram illustrating a construction of an X-ray CT apparatus consistent with one embodiment of the present invention.

FIG. 1 illustrates a construction of an X-ray CT apparatus 100 consistent with the present invention. X-ray CT apparatus 100 includes a gantry 10 for performing X-ray imaging by irradiating X-ray onto an object P, a top plate moving mechanism 20, an image processing unit 30, a display unit 40, an operation unit 50 and a system control unit 60. Gantry 10 includes an almost cylindrical opening 11 for inserting an object P placed on top plate 8, a rotation unit 12 provided on a circumference of the opening 11 for rotating around a center axis of the opening 11 in a prescribed direction, and a gantry main body 13 for rotatably supporting the rotation unit 12. A rotation frame 19 in the rotation unit 12 is rotated in a prescribed direction, for instance, the R1 direction, by a rotation mechanism 13a provided in the gantry main body 13. The rotation frame 19 is fixed to a main frame through main bearings.

Top plate moving mechanism 20 moves the top plate 8 in an elongate direction along the axis of the opening, and in up and down directions. Image processing unit 30 generates image data by performing reconstruction of X-ray projection data generated in the gantry 10. Display unit 40 displays image data generated by the image processing unit 30. Operation unit 50 performs input operations such as setting of X-ray irradiation conditions for examining the object P and inputting examination data including the object data. System control unit 60 totally controls the gantry 10, the top plate moving mechanism 20, the image processing unit 30 and the display unit 40.

On the rotation unit 12 in the gantry, an X-ray generation unit 14 and an X-ray detection unit 15 are provided facing each other through the opening 11. X-ray generation unit 14 irradiates X-rays onto the object P and the X-ray detection unit 15 detects X-rays penetrated through the object P.

Gantry 10 further includes a data acquisition unit 16, a data transmission unit 17, a high voltage generation unit 18 and a rotation frame 19. Data acquisition unit 16 generates X-ray projection data X-ray projection data by acquiring detection signals from the X-ray detection unit 15. Data transmission unit 17 transmits X-ray projection data generated in the data acquisition unit 16 to the image processing unit 30 in the X-ray CT apparatus 100. High voltage generation unit 18 supplies a high voltage necessary for irradiating X-rays to the X-ray generation unit 14. The X-ray generation unit 14, X-ray detection unit 15, data acquisition unit 16, data transmission unit 17, and high voltage generation unit 18 are held on the rotation frame 19.

X-ray generation unit 14 includes an X-ray tube for generating X-rays and a slit for setting a scope of X-ray irradiation. X-ray generation unit 14 irradiates fan-shaped X-rays having a fan angle θ with centering at a convergence point of the X-ray tube. X-ray generation unit 14 and X-ray detection unit 15 are rotated around the object placed into the opening 11.

Figure 2:
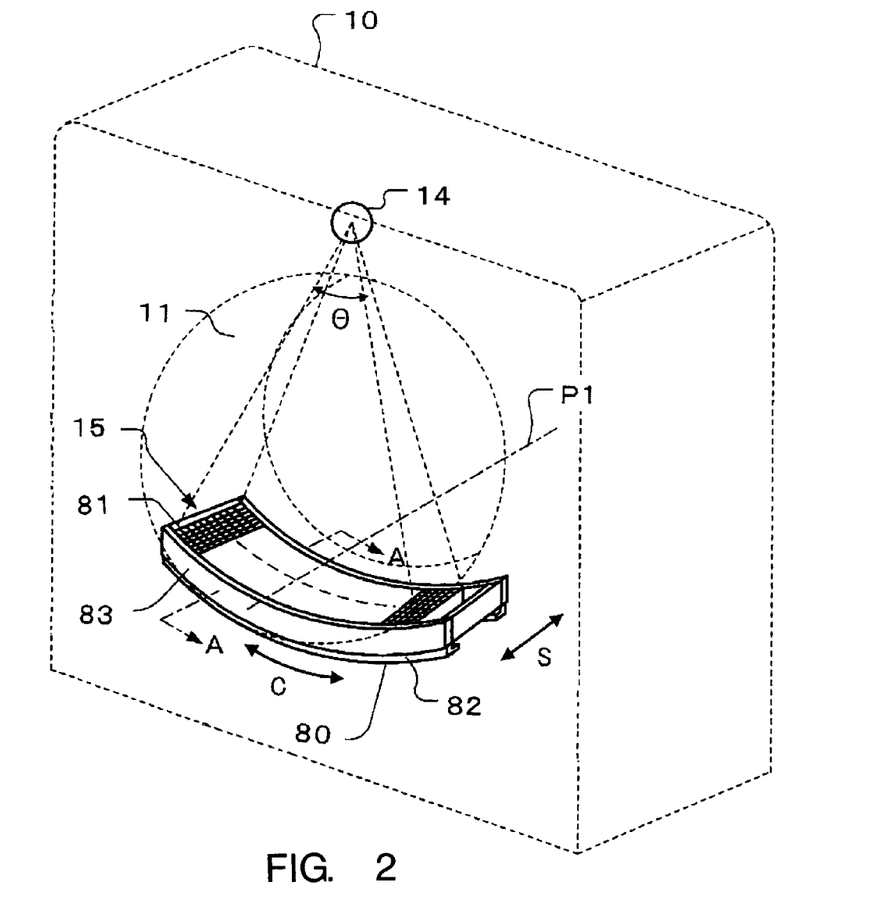
FIG. 2 is a perspective view of an X-ray detection unit provided in a gantry of the X-ray CT apparatus shown in FIG. 1.

FIG. 2 illustrates the X-ray detection unit 15 provided in the gantry 10 of the X-ray CT apparatus 100. For detecting X-rays penetrated through the object P, X-ray detection unit 15 is oriented facing the X-ray generation unit 14 through the opening 11. X-ray detection unit 15 includes a plurality (n) of detection packs 80 arranged in a generally circular arc-shape along a rotation direction of the rotation unit 12. In the following explanation, an arrangement of the X-ray detection unit 15 along a circular arc direction with a fan angle θ from X-ray generation unit 14 is referred to as a channel (C) direction. Further, an arrangement in the X-ray detection unit 15 along a body axis P1 of the object P in the opening 11 is referred to as a slice (S) direction. Thus, the slice (S) is perpendicular to the channel (C) direction.

Each of the plurality of detection packs 80 includes a plurality of collimators 81 for restricting incidence of scattered X-rays, a detection pack holding unit 82 for holding the plurality of detection packs 80 arranged in the channel direction, a collimator 81 and a supporting body 83 for supporting the detection pack holding unit 82. The supporting body 83 is held on the rotation frame 19 shown in FIG. 1.

Each detection pack 80 converts the detected X-rays to electric signals and outputs the converted signals to the data acquisition unit 16. After converting analog signals output from the X-ray detection unit 15 to digital signals, the data acquisition unit 16 acquires one view X-ray projection data by rotating the rotation frame 19 in the channel direction at a prescribed imaging rotation angle.

Data transmission unit 17 includes a transmission unit and a reception unit for transmitting and receiving data, for example by using light guides. The transmission unit in the data transmission unit 17 is provided in the rotation unit 12. X-ray projection data acquired in the data acquisition unit 16 is transferred to the reception unit of the data transmission unit 17 provided on the gantry main body 13.

Image processing unit 30 in the X-ray CT apparatus 100 includes a memory 31 for storing X-ray projection data output from data transmission unit 17 in the gantry 10 and an image data generation unit 32 for generating image data by reconstructing X-ray projection data stored in the memory 31.

Image data generation unit 32 in the image processing unit 30 generates image data by reconstructing X-ray projection data of a plurality of views generated at every imaging angle during one scan. By one scan is meant an imaging operation during a rotation of a prescribed angle of, for instance, less than 360 degrees that is obtained by adding a 180 degrees rotation angle of the rotation frame 19 and a fan angle θ.

Display unit 40 includes a monitor such as an LCD (liquid crystal display) panel or a CRT (cathode ray tube) for displaying image data output from the image data generation unit 32.

Operation unit 50 is an interactive interface having input devices, such as a key board, a track ball, joy stick, or a mouse, a display panel and various switches for inputting object data and X-ray irradiation conditions.

System control unit 60 includes a CPU (central processing unit) and a memory circuit for storing input data supplied from the operation unit 50. Based on the input data, system control unit 60 controls operations such as generation of X-ray projection data, generation and display of image data and miscellaneous control of various mechanisms.

Figure 3:
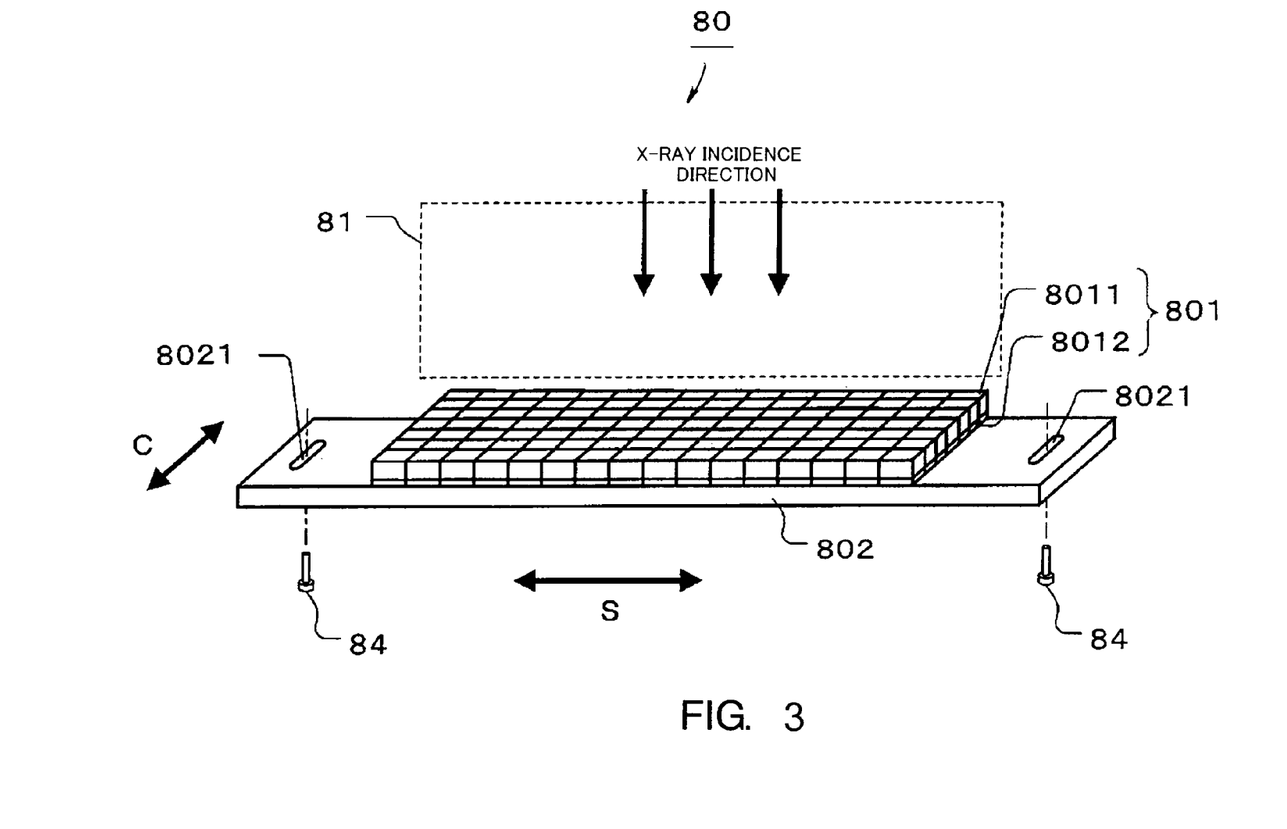
FIG. 3 is a perspective view of a detection pack used in the X-ray detection unit shown in FIG. 2.

FIG. 3 illustrates each construction of the detection pack 80 in the X-ray detection unit 15 shown in FIG. 2. A plurality (n) of detection packs 80 are arranged on a circular arc configuration of a fan angle θ that has a center at a convergence point of X-ray tube in the X-ray generation unit 14. As illustrated in FIG. 3, each detection pack 80 includes a plurality of detecting elements 801 arranged in both a slice direction and a channel direction and a rectangular board 802 for supporting the plurality of detecting elements 801 as an integrated body.

Each detecting element 801 on the board 802 includes a scintillator 8011 for converting incident X-ray on a surface through a collimator 81 to light, and a photo-diode 8012 provided between the scintillator 8011 and the board 802 for converting light supplied from the scintillator 8011 to an electric signal. The rectangular board 802 has an elongated aperture 8021 along a width direction provided near each of edges in a longitudinal direction. Each elongated aperture 8021 penetrates the board 802 for detachably fixing the board 802 on a guide rail 821 by a detachable tight fitting member 84. The detachable tight fitting member may have substantially the same function as a screw.

Figure 4:
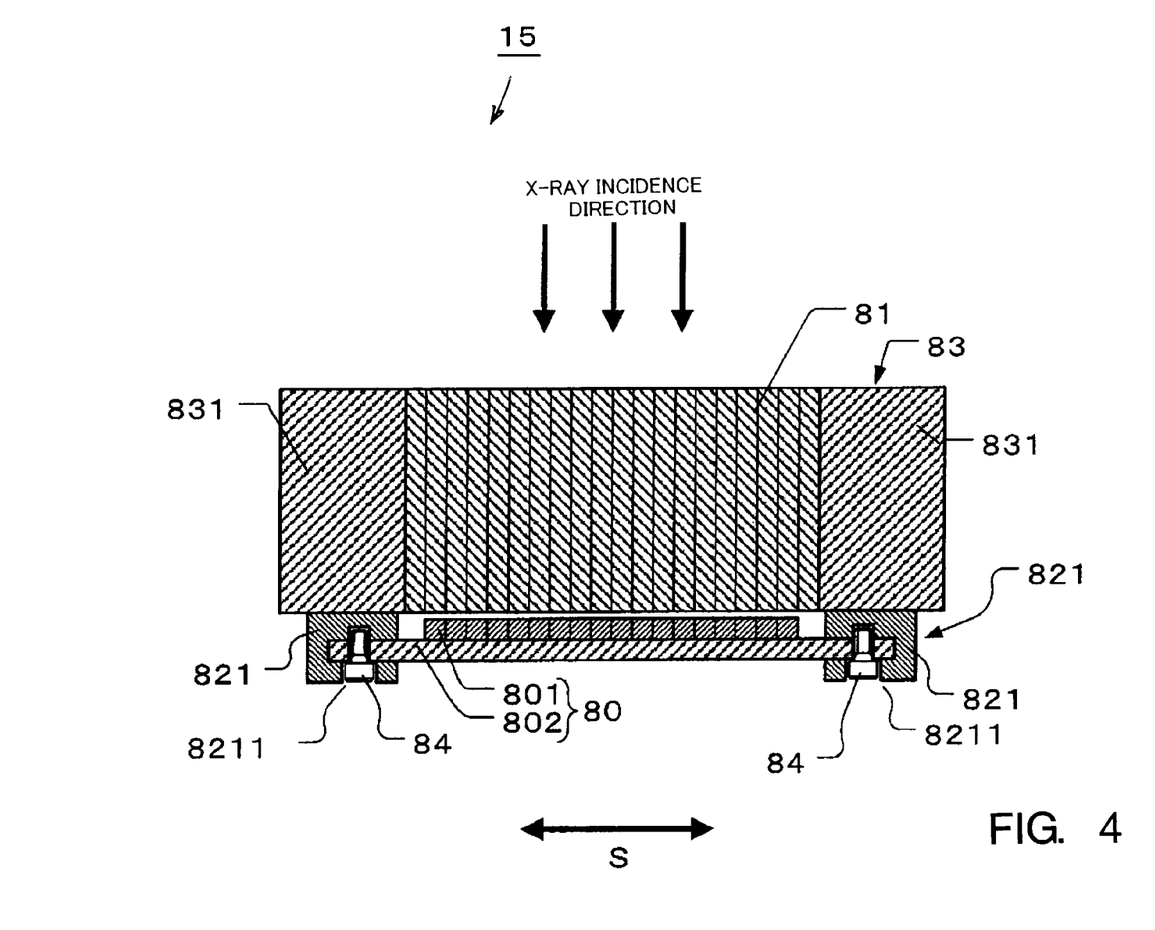
FIG. 4 is a cross-sectional view of the X-ray detection unit shown in FIG. 2 cut along A-A line.

FIG. 4 is a cross-sectional view of the X-ray detection unit 15 cut in A-A direction shown in FIG. 2. Collimator 81 is perpendicularly arranged on each surface of the detecting elements 801. Both slice directional edge portions of the collimator 81 are supported by a pair of supporting body 83. Each collimator supporting body 83 is fixed to a respective guide rail 821. The rectangular board 802 of detection pack 80 is detachably fixed to the guide rail 821 by a detachable tight fitting member 84, such as a screw, through the elongated hole 8211. Each of the pair of guide rails 821 includes a board insertion groove to hold a respective edge of the board 802.

Figure 5:
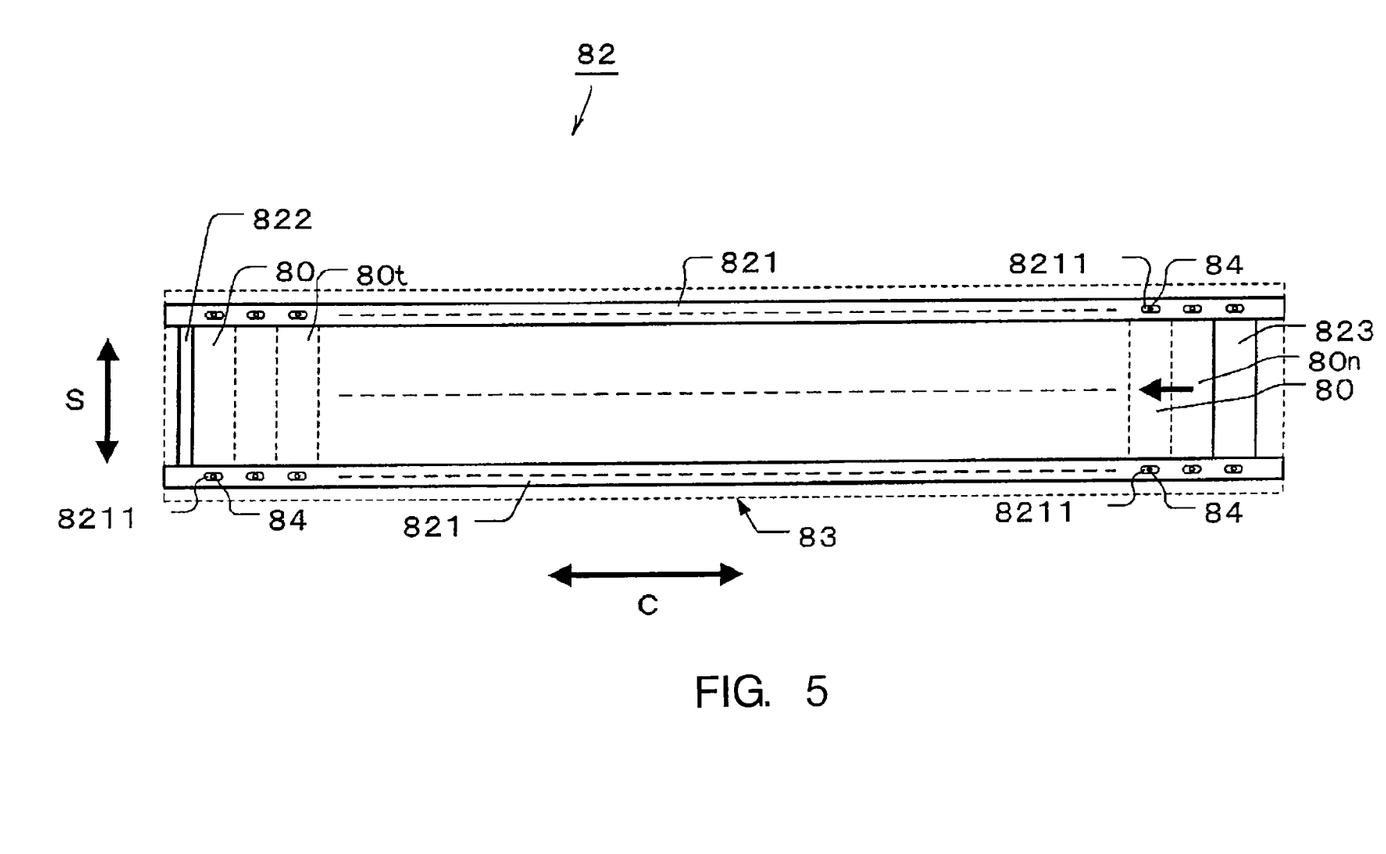
FIG. 5 is a back-side view of the detection pack holding unit used in the X-ray detection unit shown in FIG. 1.

FIG. 5 illustrates a back-side of the detection pack holding unit 82 shown in FIG. 2. Detection pack holding unit 82 includes a pair of circular arc-shaped guide rails 821 at both edges along the channel (C) direction. Each of the pair of guide rails includes a plurality (n+1) of elongated holes 8211 that penetrate an outer surface of the guide rail and the board insertion groove. The guide rails 821 prohibit a moving of each detection pack 80 in the slice (S) direction, and also hold each detection pack 80 so as to freely move in the channel (C) direction.

At one end portion of the circular arc-shaped guide rail 821, a reference positioning plate 822 is fixed on the collimator supporting body 83 for deciding a reference position in the channel direction of the detection pack 80 held on the guide rail 821. The other end portion of the circular arc-shaped guide rail 821 is provided with a pressing board 823 detachably provided at the other end portion. The pressing board 823 presses the plurality of detection packs 80 toward the reference positioning plate 822 so as to put into contact edges of adjacent detection packs 80.

The pair of guide rails 821 provided at slice directional edges of the detection pack holding unit 82 are placed apart by a longitudinal length of the board 802 of the detection pack 80 so as to face each other. Further, as mentioned above, a plurality (n+1) of elongated holes 8211 are provided on an outer surface of the guide rail in a circular arc direction. The board 802 of each detection pack 80 is fixed to the pair of guide rails 821 by a detachable tight fitting member 84 through the elongated holes 8211 and the grooves.

Pressing board 823 is constructed similar to the board 802 of the detection pack 80. Thus, pressing board 823 includes an elongated hole in each longitudinal edge portion. Further, the pressing board 823 includes a spring member (not shown) on an edge facing an edge of the detection pack 80 arranged lastly on guide rail 821.

Pressing board 823 is fixed to the guide rail 821 at a pressed position of the last detection pack 80 pressed by a detachable tight fitting member 84, such as a screw. The screw is detachably provided so as to penetrate the elongated hole 8211 at the edge portion of the guide rail 821.

Figure 6:
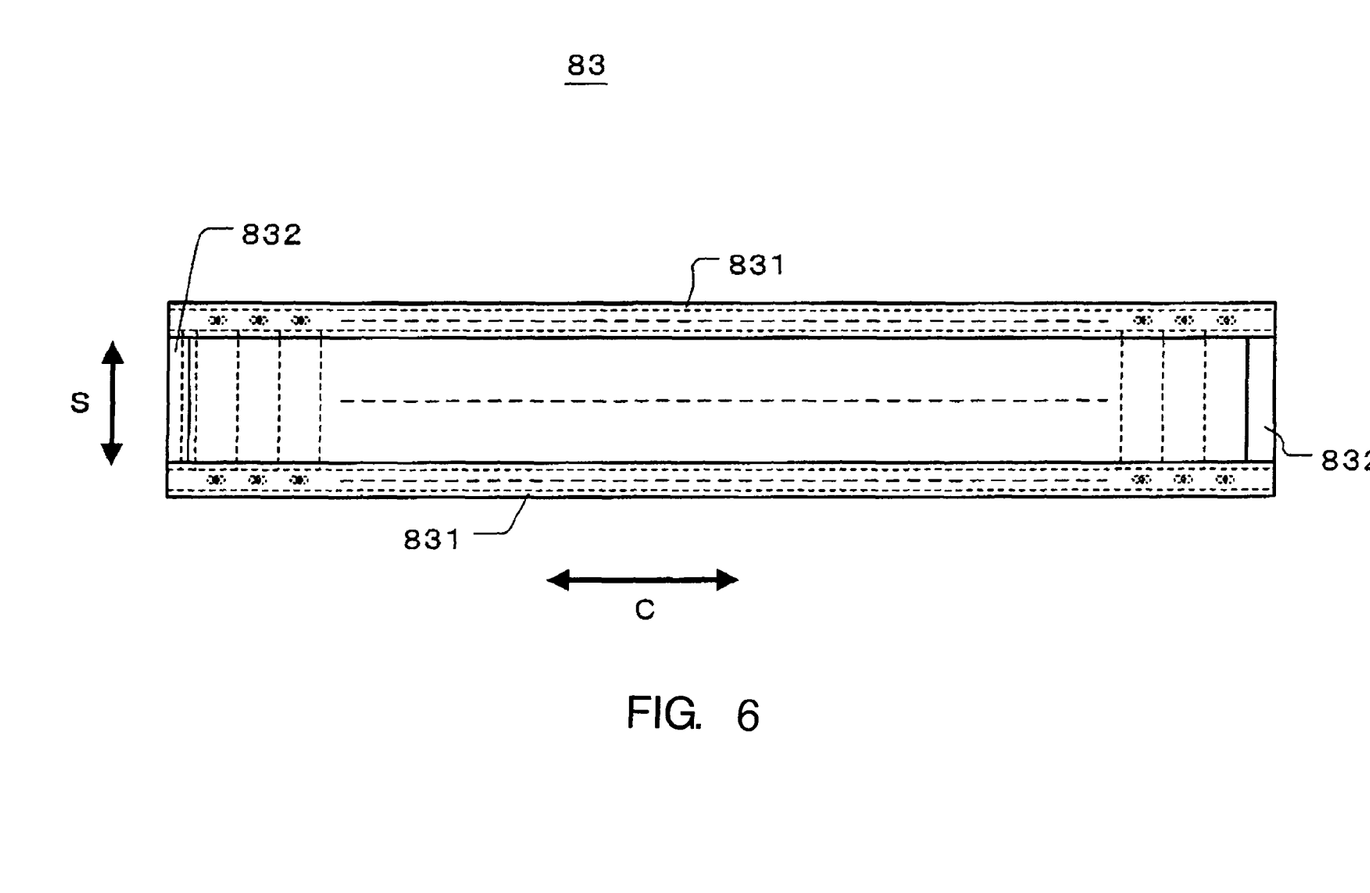
FIG. 6 is a back-side view of the collimator holding body used in the X-ray detection unit shown in FIG. 4.

As illustrated in FIG. 6, the collimator supporting body 83 includes a pair of opposed circular arc-shaped elongate boards 831 and a pair of short side boards 832 provided at each end portion of the elongate board 831 so as to be perpendicular to the elongate board 831. Each elongate board 831 supports the collimator 81 at a facing side and also supports each guide rail 821 of detection pack holding unit 82 at a circular arc-shaped outer surface.

Installation of the plurality of detection packs 80 to the detection pack holding unit 82 is performed as next described. Firstly, a first detection pack 80₁ is moved on the guide rail 821 so as to contact the reference positioning plate 822 with both edges freely held along the longitudinal direction of the detection pack 80₁ in the guide rail 821. Then, like the first detection pack 80₁, the plurality (n−1) of detection packs 80 are successively moved on the guide rail 821 so as to be arranged in a line in contact with each other.

Thus, it becomes possible to decide each position of the plurality of detection packs 80 in a channel direction by moving the first detection pack 80 on the guide rail 821 so as to contact the reference positioning plate 822 and by moving the following detection packs 80 so as to contact each other. Further, it becomes possible to decide a position of each detection pack in a slice direction by holding both edges of the respective detection packs 80 in the pair of guide rails 821.

After arranging the plurality of detection packs 80, a pressing board 823 having edges fitted in the grooves of the guide rails 821 is mounted on the guide rails 821. The pressing board 823 is fixed to the guide rail 821 by using a detachable tight fitting member 84 with spring loaded contact with the lastly installed detection pack 80, on the guide rail 821. After fixing the pressing board 823 on the guide rail 821, each of the plurality of detection packs 80 is successively fixed on the guide rails 821 by detachable tight fitting members 84.

Thus, it becomes possible to reduce a gap between adjacent detection packs 80 to less than a channel pitch of a high-resolution detecting element by pressing the lastly installed detection pack 80$_n$ by the pressing board 823. Thus, it becomes possible to stably hold the plurality of detection packs while substantially eliminating gaps between adjacent detection packs.

While each of the plurality of detection packs is fixed by a detachable tight fitting member in the above-mentioned embodiment, since the pressing board presses the plurality of detection packs, it is also possible only to fix the pressing board 823 on the guide rails 821. In such a case, a reference positioning plate 822 is provided at a position where receives inertial force affecting to the plurality of detection packs during a rotation of rotation unit in the gantry 10.

Figure 7:
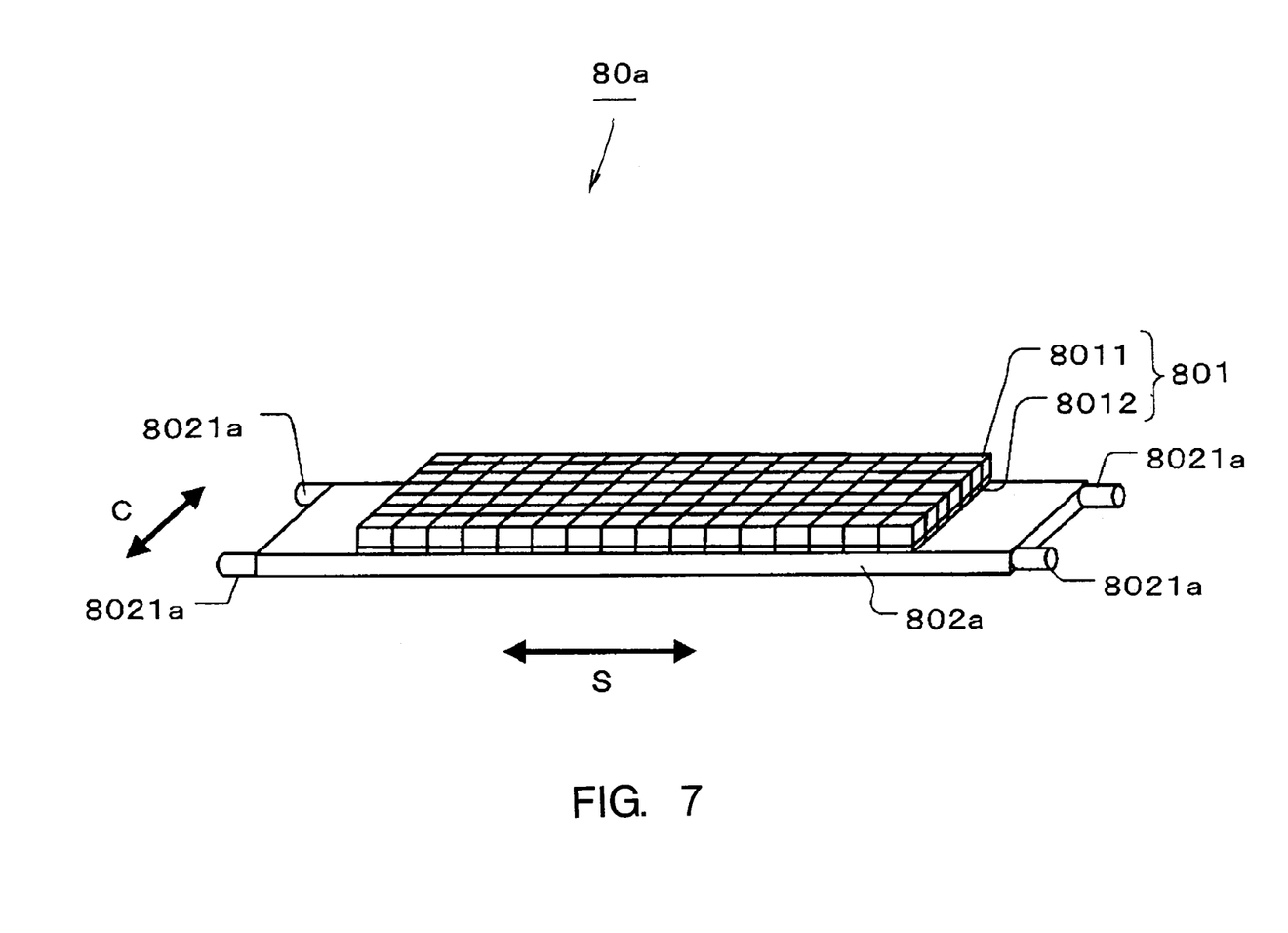
FIG. 7 is a perspective view of another embodiment of the detection pack used in the X-ray detection unit.

FIG. 7 illustrates another embodiment of a detection pack 80a that is suitable for fixing a plurality of detection packs only by a press board 823. The detection pack 80a is constructed by providing a pair of guide rail coupling bars 8021a on each edges of board 802a for installing the detection pack 80a on the guide rail 821. This board edge is constructed by cutting out a part of the edge portion of the board 802 shown in FIG. 3. By sliding the guide rail coupling bar 8021a on the guide rails 821, smooth movement of the detection pack 80a on the guide rails 821 can be obtained.

After fixing the plurality of detections pack 80 on the guide rails 821, it is also possible to remove the pressing board 823 from the guide rails 821. Then, each detection pack 80 is fixed on the guide rails 821 by using only a fastener such as the screw 84.

For a maintenance operation or a repair of the X-ray detection unit 15, the detection pack 80 needs to be exchanged. In case of the detection pack 80 as shown in FIG. 5, firstly, the pressing board 823 is removed from the guide rails 821 by detaching the screw 84. Next, each of screws 84 for the respective detection packs is detached for moving and detaching each of detection packs from the lastly mounted detection pack 80n to a target detection pack 80t. Then, the last detection pack 80n is removed from the guide rails 821 and the successive target detection packs are removed until removing the target detection pack 80t from the guide rails 821 for exchange.

An exchanged new detection pack is mounted and moved on the guide rails 821 until contacting the fixed detection pack remaining next to the target detection pack 80t. Then the removed detection packs other than the exchanged target detection pack 80t are again mounted and moved on the guide rails 821 for placing at the respective original positions. After finishing the exchange, the pressing board 823 is fixed on the guide rails 821 to press the re-installed detection packs. Each of the re-installed detection packs is fixed on the guide rails 821 at each of the original positions by the detachable tight fitting member, depending on the necessity.

Figure 8:
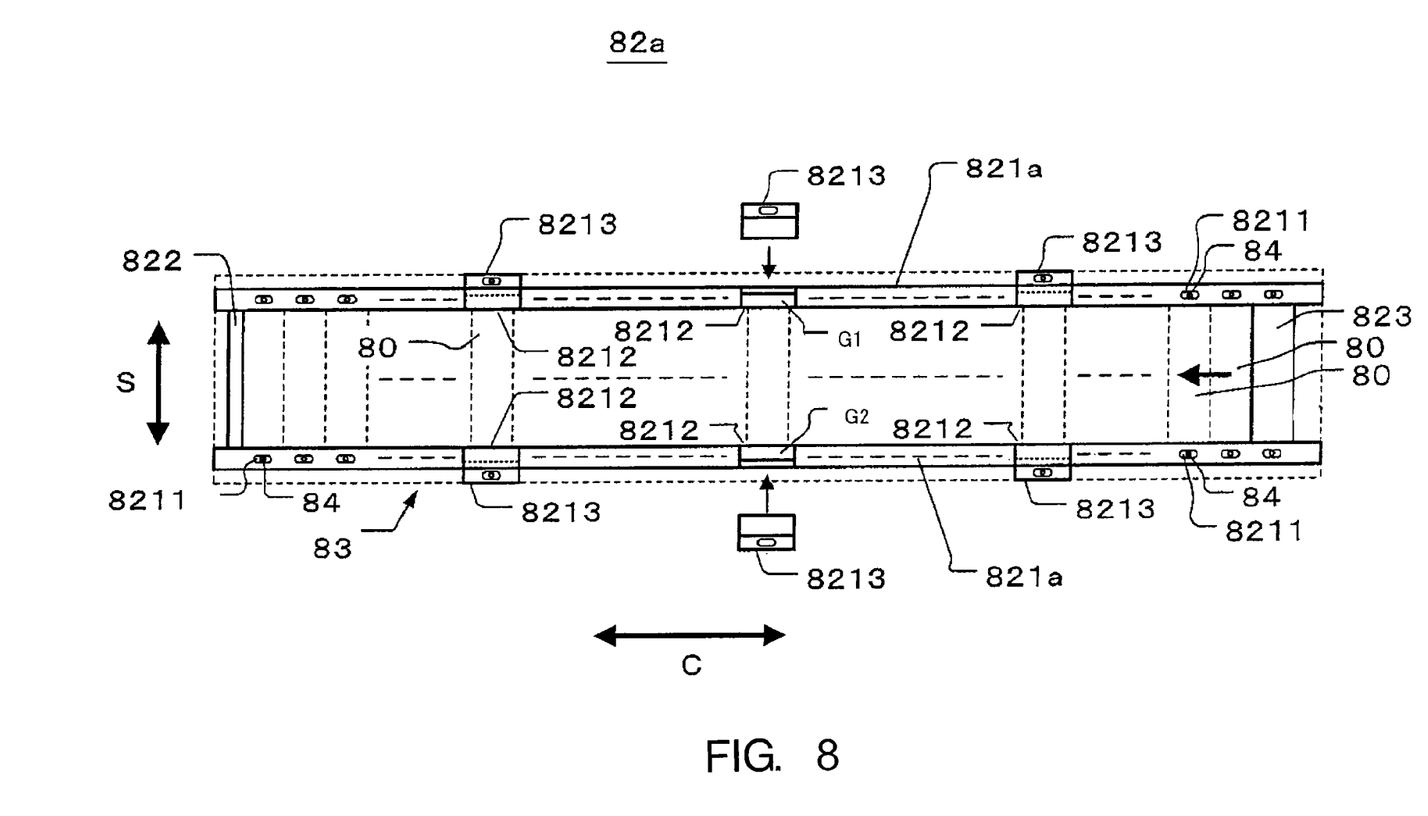
FIG. 8 is a back-side view of another embodiment of the detection pack holding unit used in the X-ray detection unit.

FIG. 8 illustrates a back-side view of the detection pack holding unit 82a. As illustrated in FIG. 8, a pair of guide rails 821a of the detection pack holding unit 82a includes a plurality pair of notches 8212 on the guide rail 821a at a prescribed interval so as to reach to each outer surface of the grooves G1, G2 provided on the guide rail 821a. Each notch 8212 is detachably covered by a hold cover 8213.

When a detection pack is exchanged for maintenance, a hold cover 8213 covering a notch 8212 provided near the target detection pack 80t is removed, and the target detection pack 80t is detached through the notch 8212. After installing the exchanged detection pack 80t on the guide rails 821a through the notch 8212, the covering hold cover 8213 is fixed on the supporting body 83 by a detachable tight fitting member 84.

According to this embodiment, it becomes possible to reduce maintenance time by avoiding long removal of the target detection pack 80t on the guide rail 821a for an exchange.

According to the above-mentioned embodiments, it becomes possible to easily decide each position of the detection packs in the slice direction by mounting each detection pack on the guide rail. Further, it becomes possible to accurately decide each position of the detection packs in the channel direction by successively contacting pressure edges of adjacent detection pack towards reference positioning plate 822 by the spring loaded pressing board 823.

Further, the above-mentioned embodiments can provide a high-resolution and a high-performance X-ray detection apparatus by reducing gaps between adjacent detection packs. To reduce a gap between two detection packs, the pressing board 823 is mounted so as to press the lastly held detection pack on the guide rail towards reference positioning plate. By fixing each detection pack on the guide rail through screws, positions of the detection packs are stably kept with reduced gap between adjacent detection packs. Consequently, resolution of image data can be improved with avoidance of lack of image data corresponding to the gaps.

Other embodiments consistent with the present invention will be apparent to those skilled in the art from consideration of the specification and practice of the present invention disclosed herein. It is intended that the specification and examples be considered as exemplary only, with a true scope and spirit of the present invention being indicated by the following claims.

The invention claimed is:

1. An X-ray detecting apparatus for detecting X-ray amounts penetrated through an object by irradiating an X-ray beam on the object, the X-ray detecting apparatus comprising:
   a plurality of detection packs successively arranged in an arrangement direction and configured to detect the X-ray amounts penetrated through the object;
   a pair of guide rails configured to hold the plurality of detection packs so as to freely move each of the plurality of detection packs in the arrangement direction of the plurality of detection packs; and
   a fixing unit provided on each of the pair of guide rails to detachably fix the plurality of detection packs so that adjacent edges of the detection packs next to each other contact each other,
   wherein the fixing unit comprises:
   a positioning plate provided near to one end of the pair of guide rails for deciding a stop position of the plurality of detection packs held by the pair of guide rails and so as to prohibit movement of the plurality of detection packs in the arrangement direction.

2. An X-ray CT apparatus comprising:
   a gantry;
   an X-ray source provided in the gantry so as to irradiate an X-ray beam on an object placed at a center portion of the gantry;
   a multi-slice X-ray detection unit provided in the gantry and located opposite the X-ray source so as to detect X-ray amounts penetrated through the object;
   wherein the multi-slice X-ray detection unit comprises:
   a plurality of multi-slice detection packs successively arranged in a channel direction of the X-ray beam to detect X-rays penetrated through the object,
   a pair of guide rails configured to freely move the plurality of multi-slice detection packs in the channel direction, and
   a fixing unit held by the pair of guide rails to fix the plurality of detection packs on the pair of guide rails with edges of adjacent detection packs in contact with each other,
   wherein the fixing unit comprises:
   a positioning plate provided near to one end of the pair of guide rails for deciding a stop position of the plurality of detection packs held by the pair of guide rails and so as to prohibit movement of the plurality of detection packs in the channel direction.

3. The X-ray CT apparatus according to claim 2, wherein the fixing unit further comprises:
a pressing member configured to press the lastly mounted detection pack at another end of the pair of guide rails.

4. The X-ray CT apparatus according to claim 2, wherein the fixing unit further comprises:
a detachable tight fitting member inserted through an elongated hole provided on each of the plurality of detection packs in the channel direction.

5. The X-ray CT apparatus according to claim 2, wherein each of the pair of guide rails includes a plurality of notches for removing the detection packs, and a plurality of covers for detachably covering each of the plurality of notches.

6. An X-ray CT apparatus comprising:
a gantry;
an X-ray source provided in the gantry so as to irradiate an X-ray beam on an object placed at a center portion of the gantry;
a multi-slice X-ray detection unit provided in the gantry and located opposite the X-ray source so as to detect X-ray amounts penetrated through the object;
wherein the multi-slice X-ray detection unit comprises:
a plurality of multi-slice detection packs successively arranged in a channel direction of the X-ray beam to detect X-rays penetrated through the object,
a pair of guide rails configured to freely move the plurality of multi-slice detection packs in the channel direction, and
a fixing unit held by the pair of guide rails to fix the plurality of detection packs on the pair of guide rails with edges of adjacent detection packs in contact with each other,
wherein each of the pair of guide rails includes a plurality of notches for removing the detection packs, and a plurality of covers for detachably covering each of the plurality of notches.

7. An X-ray CT apparatus according to claim 6, wherein the fixing unit comprises:
a positioning plate provided near to one end of the pair of guide rails for deciding a stop position of the plurality of detection packs held by the pair of guide rails and so as to prohibit movement of the plurality of detection packs in the channel direction.

8. The X-ray CT apparatus according to claim 7, wherein the fixing unit comprises:
a pressing member configured to press the lastly mounted detection pack at another end of the pair of guide rails.

9. The X-ray CT apparatus according to claim 6, wherein the fixing unit comprises:
a detachable tight fitting member inserted through an elongated hole provided on each of the plurality of detection packs in the channel direction.

* * * * *